US008884088B2

(12) United States Patent
Smith et al.

(10) Patent No.: US 8,884,088 B2
(45) Date of Patent: Nov. 11, 2014

(54) DEHYDROGENATION PROCESS

(75) Inventors: Charles M. Smith, Houston, TX (US);
Tan-Jen Chen, Kingwood, TX (US);
Terry E. Helton, Bethlehem, PA (US);
Teng Xu, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 1 day.

(21) Appl. No.: 13/510,579

(22) PCT Filed: Dec. 17, 2010

(86) PCT No.: PCT/US2010/061006
§ 371 (c)(1),
(2), (4) Date: Jul. 20, 2012

(87) PCT Pub. No.: WO2011/096991
PCT Pub. Date: Aug. 11, 2011

(65) Prior Publication Data
US 2012/0283494 A1 Nov. 8, 2012

Related U.S. Application Data

(60) Provisional application No. 61/334,787, filed on May 14, 2010, provisional application No. 61/334,784, filed on May 14, 2010, provisional application No. 61/301,799, filed on Feb. 5, 2010, provisional application No. 61/301,794, filed on Feb. 5, 2010.

(30) Foreign Application Priority Data

Jun. 16, 2010 (EP) .................................. 10166168

(51) Int. Cl.
*C07C 5/367* (2006.01)
*C07C 2/74* (2006.01)
*C07C 5/31* (2006.01)

(52) U.S. Cl.
CPC ...... *C07C 2/74* (2013.01); *C07C 5/31* (2013.01); *C07C 5/367* (2013.01); *C07C 2101/08* (2013.01); *C07C 2101/14* (2013.01); *C07C 2521/04* (2013.01); *C07C 2521/06* (2013.01); *C07C 2521/08* (2013.01); *C07C 2521/12* (2013.01); *C07C 2521/16* (2013.01); *C07C 2523/06* (2013.01); *C07C 2523/14* (2013.01); *C07C 2523/42* (2013.01); *C07C 2523/44* (2013.01); *C07C 2523/46* (2013.01); *C07C 2523/58* (2013.01); *C07C 2523/75* (2013.01); *C07C 2523/755* (2013.01); *C07C 2527/173* (2013.01); *C07C 2529/08* (2013.01); *C07C 2529/40* (2013.01); *C07C 2529/65* (2013.01); *C07C 2529/70* (2013.01); *C07C 2529/83* (2013.01); *C07C 2529/85* (2013.01)
USPC ............................ 585/319; 585/440; 585/700

(58) Field of Classification Search
USPC ........................................ 585/319, 440, 700
See application file for complete search history.

(56) References Cited

U.S. PATENT DOCUMENTS

| 3,293,192 A | 12/1966 | Maher et al. |
| 3,308,069 A | 3/1967 | Wadlinger et al. |
| 3,402,996 A | 9/1968 | Maher et al. |
| 3,412,165 A | 11/1968 | Slaugh et al. |
| 3,702,886 A | 11/1972 | Argauer et al. |
| 3,709,979 A | 1/1973 | Chu |
| 3,761,428 A | 9/1973 | Sugier et al. |
| RE28,341 E | 2/1975 | Wadlinger et al. |
| 3,962,362 A | 6/1976 | Suggitt |
| 4,094,918 A | 6/1978 | Murtha et al. |
| 4,122,125 A | 10/1978 | Murtha et al. |
| RE29,948 E | 3/1979 | Dwyer et al. |
| 4,147,726 A | 4/1979 | Wu |
| 4,177,165 A | 12/1979 | Murtha et al. |
| 4,206,082 A | 6/1980 | Murtha et al. |
| 4,439,409 A | 3/1984 | Puppe et al. |
| 4,501,926 A | 2/1985 | LaPierre et al. |
| 4,826,667 A | 5/1989 | Zones et al. |
| 4,870,217 A | 9/1989 | Knifton |
| 4,891,458 A | 1/1990 | Innes et al. |
| 4,954,325 A | 9/1990 | Rubin et al. |
| 5,053,571 A | 10/1991 | Makkee |
| 5,236,575 A | 8/1993 | Bennett et al. |

(Continued)

FOREIGN PATENT DOCUMENTS

| GB | 720064 | 12/1954 |
| JP | 54-099788 | 8/1979 |
| WO | 2009/131769 | 10/2009 |

OTHER PUBLICATIONS

Gault, "*Mechanisma of Skeletal Isomerization of Hydrocarbons on Metals*", Advances in Catalysis, 1981, vol. 30, pp. 1-95.
Gonzales-Cortes et al., "*Tuning the Ring-Opening Reaction of 1,3-dimethylcyclohexane with the Addition of Potassium Over Ir-Containing Catalysts*", Chemical Engineering Journal, 2008, vol. 139, pp. 147-156.
Soled et al., "*Supported Metal Catalysts: Some Interesting New Leads in an Old Field*", Scientific Bases for the Preparation of Heterogeneous Catalysts, 2006, vol. 162, pp. 103-110.
Borodina et al., "*Hydroalkylation of Benzene and Ethylbenzene Over Metal Containing Zeolite Catalysts*", Microporous and Mesoporous Materials, 2007, vol. 105, No. 1-2, pp. 181-188.
Du et al., "*The Chemistry of Selective Ring-Opening Catalysts*", Applied Catalysis A: General, 2005, vol. 294, No. 1, pp. 1-21.

(Continued)

Primary Examiner — Thuan D Dang
(74) Attorney, Agent, or Firm — Jamie L. Sullivan; Siwen Chen

(57) ABSTRACT

In a dehydrogenation process a hydrocarbon stream comprising at least one non-aromatic six-membered ring compound and at least one five-membered ring compound is contacted with a first catalyst comprising at least one metal component and at least one support and a second catalyst. The first catalyst is utilized to convert at least a portion of the at least one non-aromatic six-membered ring compound in the hydrocarbon stream to at least one aromatic compound and the second catalyst is utilized to convert at least a portion of the at least one five-membered ring compound in the hydrocarbon stream to at least one paraffin.

19 Claims, No Drawings

(56) References Cited

U.S. PATENT DOCUMENTS

| | | | |
|---|---|---|---|
| 5,250,277 | A | 10/1993 | Kresge et al. |
| 5,362,697 | A | 11/1994 | Fung et al. |
| 5,811,624 | A | 9/1998 | Hantzer et al. |
| 5,906,729 | A | 5/1999 | Chou |
| 6,037,513 | A | 3/2000 | Chang et al. |
| 6,077,498 | A | 6/2000 | Diaz Cabanas et al. |
| 6,720,462 | B2 | 4/2004 | Kuhnle et al. |
| 6,756,030 | B1 | 6/2004 | Rohde et al. |
| 7,563,358 | B2 | 7/2009 | Stavens et al. |
| 7,579,511 | B1 * | 8/2009 | Dakka et al. ............ 585/316 |
| 7,605,107 | B2 | 10/2009 | Soled et al. |
| 8,247,627 | B2 | 8/2012 | Dakka et al. |
| 2003/0083527 | A1 | 5/2003 | Kuhnle et al. |
| 2006/0166809 | A1 | 7/2006 | Malek et al. |

OTHER PUBLICATIONS

Galperin et al., "*Effect of Support Acid-Basic Properties on Activity and Selectivity of Pt Catalysts in Reaction of Methylcyclopentane Ring Opening*", Applied Catalysis A: General, 2003, vol. 239, No. 1-2, pp. 297-304.

Koel et al., "*Thermochemistry of the Selective Dehydrogenation of Cyclohexane to Benzene on Pt Surfaces*", Journal of Molecular Catalysis: A Chemical, 1998, vol. 131, pp. 39-53.

Smirniotis et al., "*Comparison Between Zeolite $\beta$ and $\gamma$-$Al_2O_3$ Supported PT for Reforming Reactions*", Journal of Catalysis, 1993, vol. 140, pp. 526-542.

Smirniotis et al., "*Increased Aromatization in the Reforming of Mixtures of N-Hexane, Methylcyclopentane and Methylcyclohexane Over Composites of Pt/BaKL Zeolite with Pt/beta or Pt/USY Zeolites*", Applied Catalysis A: General, 1995, vol. 123, No. 1, pp. 59-88.

\* cited by examiner

DEHYDROGENATION PROCESS

PRIORITY CLAIM

This application is a National Stage Application of International Application No. PCT/US2010/061006 filed Dec. 17, 2010, which claims priority to U.S. Provisional Application Ser. No. 61/301,794 filed Feb. 5, 2010; U.S. Provisional Application Ser. No. 61/301,799 filed Feb. 5, 2010; and U.S. Provisional Application Ser. No. 61/334,784 filed May 14, 2010; U.S. Provisional Application Ser. No. 61/334,787 filed May 14, 2010; and European Application Serial No. 10166168.4, filed Jun. 16, 2010, the disclosures of which are fully incorporated herein by references thereto.

CROSS REFERENCE TO RELATED APPLICATIONS

This patent application is related to U.S. Provisional Application Ser. No. 61/334,767, filed May 14, 2010; U.S. Provisional Application Ser. No. 61/334,775, filed May 14, 2010; U.S. Provisional Application Ser. No. 61/334,781, filed May 14, 2010; and U.S. Provisional Application Ser. No. 61/334,784 filed May 14, 2010, the disclosures of which are fully incorporated herein by their references.

FIELD

The present invention relates to a process for dehydrogenating hydrocarbon streams and in particular the $C_6$-rich streams produced in the hydroalkylation of benzene to produce cyclohexylbenzene.

BACKGROUND

Various dehydrogenation processes have been proposed to dehydrogenate non-aromatic six membered ring compounds. These dehydrogenation processes are typically used to convert non-aromatic compounds such as cyclohexane into aromatic compounds such as benzene wherein the aromatic compound produced may be used as a raw material in a subsequent process. Alternatively, the aromatic compound produced may be used as a raw material in the same process which produced the non-aromatic compound to be dehydrogenated. For example, the dehydrogenation of cyclohexane to benzene can be important in the hydroalkylation process for producing cyclohexylbenzene as illustrated below.

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffered from the problems that the selectivity to cyclohexylbenzene was low particularly at economically viable benzene conversion rates and that large quantities of unwanted by-products, particularly cyclohexane and methylcyclopentane, were produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a hydrogen to benzene molar ratio of about 0.01 to 100 and a weight hourly space velocity (WHSV) of about 0.01 to 100 hr$^{-1}$. The '513 patent discloses that the resultant cyclohexylbenzene can then be oxidized to the corresponding hydroperoxide and the peroxide decomposed to the desired phenol and cyclohexanone.

Not only does production of impurities such as cyclohexane and methylcyclopentane represent loss of valuable benzene feed, but also overall benzene conversion rates are typically only 40 to 60 wt % so that recycle of unreacted benzene is essential. Unless removed, these impurities will tend to build up in the recycle stream thereby displacing benzene and increasing the production of undesirable by-products. Thus a significant problem facing the commercial application of cyclohexylbenzene as a phenol precursor is removing the cyclohexane and methylcyclopentane impurities in the benzene recycle streams.

One solution to this problem is proposed in U.S. Pat. No. 7,579,511 which describes a process for making cyclohexylbenzene in which benzene undergoes hydroalkylation in the presence of a hydroalkylation catalyst to form a first effluent stream containing cyclohexylbenzene, cyclohexane, methyl cyclopentane, and unreacted benzene. The first effluent stream is then separated into a cyclohexane/methylcyclopentane-rich stream, a benzene-rich stream, and a cyclohexylbenzene-rich stream and the cyclohexane/methylcyclopentane-rich stream is contacted with a second, low acidity, dehydrogenation catalyst to convert at least a portion of the cyclohexane to benzene and at least a portion of the methylcyclopentane to linear and/or branched paraffins and form a second effluent stream. The benzene-rich stream and the second effluent stream can then be recycled to the hydroalkylation step. However, one problem with this process is that cyclohexane and methylcyclopentane have similar boiling points to that of benzene so that their separation by conventional distillation is difficult.

Another solution is proposed in International Patent Publication No. WO2009/131769, in which benzene undergoes hydroalkylation in the presence of a hydroalkylation catalyst to produce a first effluent stream containing cyclohexylbenzene, cyclohexane, and unreacted benzene. The first effluent stream is then divided into a cyclohexylbenzene-rich stream and a $C_6$ product stream comprising cyclohexane and benzene. At least part of the $C_6$ product stream is then contacted with a second catalyst under dehydrogenation conditions to convert at least part of the cyclohexane to benzene and produce a second effluent stream which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group VIII metal on a porous inorganic support such as aluminum oxide, silicon oxide, titanium oxide, zirconium oxide, activated carbon and combinations thereof. However, in practice, such a dehydrogenation catalyst has only limited activity for the conversion of methylcyclopentane and in some instances can undergo rapid aging. There is therefore a need for an improved catalyst for removing cyclohexane and methylcyclopentane from the benzene recycle streams employed in benzene hydroalkylation processes.

According to the present invention, it has now been found that a dual catalyst system is effective for the dehydrogenation of cyclohexane to benzene and conversion of methylcyclopentane to linear and/or branched paraffins in hydrocarbon streams in that the dual catalyst system offers higher conversion of methylcyclopentane than a single catalyst dehydrogenation system.

SUMMARY

In one aspect, the invention resides in a dehydrogenation process comprising:
(a) providing a hydrocarbon stream comprising at least one non-aromatic six-membered ring compound and at least one five-membered ring compound;
(b) producing a first reaction product stream comprising the step of contacting at least a portion of the hydrocarbon stream with a first catalyst comprising at least one support and at least one metal component and under conditions effective to convert at least a portion of the at least one non-aromatic six-membered ring compound to at least one aromatic compound; and
(c) producing a second reaction product stream comprising the step of contacting at least a portion of the first reaction product with a second catalyst and under conditions to convert at least a portion of the at least one five-membered ring compound to at least one paraffin.

Conveniently, the first catalyst comprises at least one metal component selected from Groups 6 to 10 of the Periodic Table of the Elements, especially platinum, palladium, ruthenium, nickel, zinc, tin, and cobalt.

Conveniently, the first catalyst has an alpha value of less than 10 or less than 5.

Conveniently, the second catalyst has an alpha value of more than 10 or more than 20.

In one embodiment, the hydrocarbon stream is a $C_6$-rich stream comprising benzene, cyclohexane, and methylcyclopentane.

Conveniently, $C_6$-rich stream is produced by:
(i) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene; and
(ii) separating at least a portion of the hydroalkylation reaction product stream into the $C_6$-rich stream and a cyclohexylbenzene-rich stream.

In another aspect, the invention resides in a process for producing cyclohexylbenzene, the process comprising:
(i) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and unreacted benzene;
(ii) separating at least a portion of the hydroalkylation reaction product stream into a $C_6$-rich stream comprising benzene, cyclohexane, and methylcyclopentane and a cyclohexylbenzene-rich stream;
(iii) producing a first reaction product stream comprising the step of contacting at least a portion of the $C_6$-rich stream with a first catalyst comprising at least one support and at least one metal component and the contacting being conducted under conditions effective to convert at least a portion of the cyclohexane to benzene;
(iv) producing a second reaction product stream comprising the step of contacting at least a portion of the first reaction product stream with a second catalyst and under conditions to convert at least a portion of the methylcyclopentane to at least one paraffin;
(v) separating at least a portion of the second reaction product stream produced into a benzene recycle stream and a paraffins-rich stream comprising 2-methylpentane and 3-methylpentane; and
(vi) recycling at least a portion of the benzene recycle stream to the contacting step (i).

DETAILED DESCRIPTION

Described herein is a process for dehydrogenating a hydrocarbon stream comprising at least one non-aromatic six-membered ring compound and at least one non-aromatic five-membered ring compound and optionally comprising at least one aromatic compound, such as benzene. The process comprises producing a first reaction product comprising the step of contacting at least a portion of the hydrocarbon stream with a first catalyst under conditions effective to convert at least a portion of the at least one non-aromatic six-membered ring compound in the hydrocarbon stream to at least one aromatic compound and producing a second reaction product comprising the step of contacting at least a portion of the at least one five-membered ring compound with a second catalyst under conditions effective to convert at least a portion of the at least one five-membered ring compound to at least one paraffin.

In one embodiment, the hydrocarbon stream comprises at least 10 wt % benzene, at least 20 wt % benzene, at least 30 wt % benzene, at least 40 wt % benzene, at least 50 wt % benzene, at least 60 wt % benzene, at least 70 wt % benzene, and at least 80 wt % benzene. In another embodiment, the hydrocarbon stream comprises at least 1 wt % cyclohexane, at least 5 wt % cyclohexane, at least 10 wt % cyclohexane, and at least 20 wt % cyclohexane. In still another embodiment, the hydrocarbon stream comprises at least 0.05 wt % methylcyclopentane, at least 0.5 wt % methylcyclopentane, and 5 wt % methylcyclopentane.

The first catalyst employed in the present process comprises at least one metal component and at least one support. The term "metal component" is used herein to include elemental metal and a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

Suitable metal components for use in the first catalyst comprise metals from Groups 6 to 10 of the Periodic Table of the Elements, especially platinum, palladium, ruthenium, nickel, zinc, tin, cobalt and mixtures thereof. As used herein, the numbering scheme for the Periodic Table Groups is as disclosed in Chemical and Engineering News, 63(5), 27 (1985).

The first catalyst employed herein has an alpha value less than 10, less than 5, and from about 0 to about 3. The alpha value is a measure of the acidic functionality of the catalyst and is described together with details of its measurement in U.S. Pat. No. 4,106,218 and in J. Catalysis, Vol. VI, pp. 278-287 (1966) and reference is made to these for such details. Higher alpha values correspond with a more active cracking catalyst. Where necessary the alpha value of the catalyst can be adjusted by methods known in the art, for example by steaming.

Preferably, the alpha value for the first catalyst is less than about 10 or less than about 5. In other embodiments, the alpha value lower limit may be about 0, about 0.1, about 0.2, about 0.3, about 0.4, about 0.5, about 0.6, about 0.7, about 0.8, about 0.9, about 1, about 2, about 3, about 4, and about 5; and the upper alpha value limit may be about 10, about 9, about 8, about 7, about 6, about 5, about 4, about 3 and about 2 with ranges from any lower limit to any upper limit being contemplated.

Conveniently, the support employed in the first catalyst is selected from the group consisting of silica, alumina, a silicate, a molecular sieve, zirconia, carbon, and carbon nanotubes, and preferably comprises silica. Additionally, the molecular sieve may be selected from aluminosilicate, an aluminophosphate, a silicoaluminophosphate, or a combination thereof. Impurities which can be present in the catalyst support (e.g., silica) are, for example, sodium salts such as sodium silicate which can be present from anywhere from 0.01 to 2 wt %.

In one embodiment, the first catalyst comprises a silica support having pore volumes and median pore diameters determined by the method of mercury intrusion porosimetry described by ASTM Standard Test D4284. The silica support may have surface areas as measured by ASTM D3663. In one embodiment, the pore volumes are in the range of from about 0.2 cc/gram to about 3.0 cc/gram. The median pore diameters are in the range from about 10 angstroms to about 2000 angstroms or from 20 angstroms to 500 angstroms; and the surface areas (m2/gram) are in the range from 10 to 1000 m2/gram or from 20 to 500 m2/gram. The support may or may not comprise a binder.

In one embodiment, the first catalyst comprises at least two metal components: (i) a metal promoter and (ii) a dehydrogenation metal. The metal promoter comprises at least one metal component selected from Group 1 and Group 2 of the Periodic Table of Elements, such that the metal promoter may comprise any combination or mixture of metal components selected from Groups 1 and 2 of the Periodic Table of Elements. Typically, the metal promoter is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, and at least 1.0 wt %. In one embodiment, the metal promoter comprises at least one metal component selected from Group 1 of the Periodic Table of Elements, such as potassium, cesium and rubidium; preferably potassium and potassium compounds. In another embodiment, the metal promoter comprises at least one metal component selected from Group 1 of the Periodic Table of Elements. In still another embodiment, the metal promoter comprises at least one metal component selected from Group 2 of the Periodic Table of Elements such as beryllium, calcium, magnesium, strontium, barium and radium; preferably calcium and magnesium. Typically, the metal promoter is present in an amount between about 0.1 and about 5 wt % of the catalyst or between about 0.2 and about 4 wt % of the catalyst or between about 0.3 and about 3 wt % of the catalyst.

In addition, the catalyst comprises a dehydrogenation component comprising at least one metal component selected from Groups 6 to 10 of the Periodic Table of Elements, such as platinum and palladium such that the dehydrogenation component may comprise any combination or mixture of metal components selected from Groups 6 to 10 of the Periodic Table of Elements. In another embodiment, the dehydrogenation component comprises at least one metal component selected from Group 10 of the Periodic Table of Elements.

Typically, the dehydrogenation component is present in an amount between about 0.1 and about 10 wt % of the catalyst such as between about 0.1 and about 5 wt % of the catalyst or between about 0.2 and about 4 wt % of the catalyst or between about 0.3 and about 3 wt % of the catalyst. In another embodiment, the metal promoter is present in an amount of at least 0.1 wt %; at least 0.2 wt %; at least 0.3 wt %; at least 0.4 wt %; at least 0.5 wt %; at least 0.6 wt %; at least 0.7 wt %; at least 0.8 wt %; at least 0.9 wt %; and at least 1.0 wt %.

The first catalyst is produced by initially treating the support, such as by impregnation, with a solution of the metal promoter, such as an aqueous solution of potassium carbonate. After drying, the treated support is calcined, normally in an oxygen-containing atmosphere, such as air, at a temperature of about 100° C. to about 700° C. for a time of about 0.5 to about 50 hours. The calcined support is then treated, again typically by impregnation, with a solution of the dehydrogenation component or a precursor thereof.

In another embodiment, the dehydrogenation component may be impregnated into the support with the aid of at least one organic dispersant. The organic dispersant may help to increase the metal dispersion of the metal promoter. The at least one organic dispersant may be used to increase the metal dispersion of the dehydrogenation component with or without the impregnation of the metal promoter into the support. The at least one organic dispersant is selected from an amino alcohol and an amino acid, such as arginine. Generally, the organic dispersant is present in an amount between about 1 and about 20 wt % of the solution.

After treatment with the dehydrogenation component, the support is again dried and calcined, normally in an oxygen-containing atmosphere, such as air, at a temperature of about 100° C. to about 600° C. for a time of about 0.5 to about 50 hours.

In an alternative embodiment, the dehydrogenation catalyst is produced by initially treating the support, such as by impregnation, with a solution containing both the metal promoter and the dehydrogenation component or a precursor thereof, optionally together with at least one organic dispersant selected from an amino alcohol and an amino acid, such as arginine. In this case, after drying, a single calcination procedure, normally in an oxygen-containing atmosphere, such as air, at a temperature of about 100° C. to about 700° C. for a time of about 0.5 to about 50 hours, is used to produce the finished catalyst.

In one embodiment, the material for the second catalyst can be a solid acid catalyst. The solid acid catalyst can be selected from such materials as molecular sieves, acidic clays, mixed metal oxides, ion-exchange resins, phosphonic acids, sulfonic acids, zirconias, silicas, sulfated zirconias, and mixtures thereof. The molecular sieve may be selected from aluminosilicate, an aluminophosphate, a silicoaluminophosphate, or a combination thereof. Generally, the molecular sieve is an aluminosilicate typically with a silicon to aluminum atomic ratio greater than 5:1 and less than 300:1.

Usually the molecular sieve will be incorporated with binder material such as clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia.

In one embodiment, the at least one molecular sieve is a large pore molecular sieve having an average pore size in excess of 7 Å or from 7 Å to 12 Å in other embodiments. Suitable large pore molecular sieves include those having the structure types VFI, LTL, MAZ, MEI, FAU, EMT, OFF, *BEA, MTW, MWW, and MOR (see IUPAC Commission of Zeolite Nomenclature and the "Atlas of Zeolite Framework Types", eds. Ch. Baerlocher, L. B. McCusker, and D. H. Olson, Elsevier, Sixth Revised Edition, 2007, which is hereby incorporated by reference). Examples of specific large pore molecular sieves include Zeolite L, Zeolite Beta, Zeolite Y, Ultrastable Y (USY), Dealuminized Y (Deal Y), Mordenite, ZSM-3, ZSM-4, ZSM-18, ZSM-20, ZSM-12, MCM-22, and faujasite. Preferred large pore zeolites are mordenite, Ultrastable Y (USY) and zeolite beta. USY is described in detail in U.S. Pat. Nos. 3,293,192 and 3,402,996; and Zeolite Beta is described in detail in U.S. Pat. No. 3,308,069 and U.S. Pat. No. Re 28,341, all of which are hereby incorporated by reference.

In another embodiment, the at least one molecular sieve is a medium pore molecular sieve having an average pore size of about 5 to about 7 Å. Suitable medium pore molecular sieves include those having the structure types MFI, MEL, MTW, EUO, MTT, HEU, FER, MFS, and TON structure type zeolites. Examples of specific intermediate pore size molecular sieves include ZSM-5, ZSM-11, ZSM-12, ZSM-22, ZSM-23, ZSM-34, ZSM-35, ZSM-38, ZSM-48, ZSM-50, and ZSM-57. Preferred medium pore zeolites are ZSM-5 and ZSM-11. ZSM-5 is described in detail in U.S. Pat. No. 3,702,886 and RE 29,948 and ZSM-11 is described in U.S. Pat. No. 3,709,979, all of which are hereby incorporated by reference.

Preferably, the alpha value for the second catalyst is greater than 10 and greater than 20 and from about 10 to about 200 and from about 20 to about 200. In other embodiments, the alpha value lower limit may be about 10, about 20, about 30, about 40, about 50, about 60, about 70, about 80, about 90, about 100 and the upper alpha value limit may be about 200, about 175, about 150, about 125, about 100, about 90, about 80, about 70, about 60, about 50, about 40, about 30 with ranges from any lower limit to any upper limit being contemplated.

The first reaction product will be produced in a first reaction zone comprising the first catalyst and the second reaction product will be produced in a second reaction zone comprising the second catalyst. In one embodiment, the different reaction zones may be contained within the same reactor vessel such as a stacked bed configuration. In another embodiment, the first and second catalyst may be contained in separate reactor vessels.

The first reaction zone is generally operated at a temperature between about 200° C. and about 750° C., such as between about 300° C. and about 500° C., a pressure between about 100 and about 7,000 kPaa, such as between about 300 and about 3000 kPaa, a weight hourly space velocity (WHSV) between about 0.2 and about 50 hr$^{-1}$, such as between about 1 and about 20 hr$^{-1}$ and a hydrogen to hydrocarbon feed molar ratio between about 0.1 and about 20, such as between about 1 and about 5.

Preferably, the temperature of the first reaction zone is from about 300° C. to about 750° C.; from about 350° C. to about 650° C.; from about 400° C. to about 550° C., from about 450° C. to about 550° C., and from about 400° C. to about 500° C. In other embodiments, the temperature lower limit may be about 350° C., about 400° C., about 430° C., about 440° C., about 450° C., about 460° C., about 470° C., about 480° C., and about 490° C.; and the upper limit temperature may be about 500° C., about 510° C., about 520° C., about 530° C., about 540° C., about 550° C., about 600° C., about 650° C., about 700° C., and about 750° C. with ranges from any lower limit to any upper limit being contemplated. In still other embodiments, the temperature lower limit may be about 500° C., about 510° C., about 520° C., about 530° C., about 540° C., and about 550° C.; and the upper limit temperature may be about 560° C., about 570° C., about 580° C., about 590° C., about 600° C., about 650° C., about 700° C., and about 750° C. with ranges from any lower limit to any upper limit being contemplated.

Preferably, the pressure of the first reaction zone is from 0 to about 300 psig (0 to 2068 kPag), 50 to 300 psig (345 to 2068 kPag), from 60 to 300 psig (414 to 2068 kPag), from 70 to 300 psig (482 to 2068 kPag), from 80 to 300 psig (552 to 2068 kPag), from 90 to 300 psig (621 to 2068 kPag), and from 100 to 300 psig (689 to 2068 kPag). In other embodiments, the temperature lower limit may be 50 psig (345 kPag), 60 psig (414 kPag), 70 psig (482 kPag), 80 psig (552 kPag), 90 psig (621 kPa), and 100 psig (689 kPag); and the upper limit temperature may be 125 psig (862 kPag), 150 psig (1034 kPag), 175 psig (1207 kPag), 200 psig (1379 kPag), 250 psig (1724 kPag), 300 psig (2068 kPag), 400 psig (2758 kPag), and 500 psig (3447 kPag) with ranges from any lower limit to any upper limit being contemplated. In still other embodiments, the temperature lower limit may be 150 psig (1034 kPag), 160 psig (1103 kPag), 170 psig (1172 kPag), 180 psig (1241 kPag), 190 psig (1310 kPag), and 200 psig (1379 kPag); and the upper limit temperature may be 250 psig (1724 kPag), 300 psig (2068 kPag), 400 psig (2758 kPag), and 500 psig (3447 kPag) with ranges from any lower limit to any upper limit being contemplated.

The second reaction zone is generally operated at about the same conditions as the first reaction zone. This is generally true when stacked bed process is utilized; however, the operating conditions can fluctuate between the first and second beds regardless of the configuration. In the separate reactor embodiment, the conditions will be within the same range of the first reaction zone, but may be different from the first reaction zone conditions.

Although the present process can be used with any hydrocarbon stream comprising, at least one non-aromatic six-membered ring compound and at least one non-aromatic five-membered ring compound, the process has particular application as part of an integrated process for the conversion of benzene to phenol. In such an integrated process the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

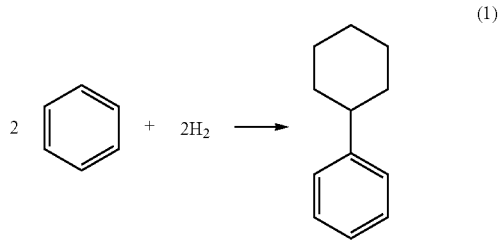 [SMILES: c1ccccc1 ; c1ccc(C2CCCCC2)cc1]

(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is generally a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain unreacted benzene feed, some dialkylated products, and other by-products, particularly cyclohexane, and methylcyclopentane. In fact, typical selectivities to cyclohexane and methylcyclopentane in the hydroalkylation reaction are 1-25 wt % and 0.1-2 wt %, respectively. The hydroalkylation reaction effluent is therefore fed to a separation system normally comprising at least two distillation towers. Given the similar boiling points of benzene, cyclohexane, and methylcyclopentane, it is difficult to separate these materials by distillation. Thus, in a distillation tower, a $C_6$-rich stream comprising benzene, cyclohexane, and methylcyclopentane is recovered from the hydroalkylation reaction effluent. This $C_6$-rich stream is then subjected to the dehydrogenation process described above such that at least a portion of the cyclohexane in the stream is converted to benzene and at least a portion of the methylcyclopentane is converted to linear and/or branched paraffins, such as 2-methylpentane, 3-methylpentane, n-hexane, and other hydrocarbon components such as isohexane, $C_5$ aliphatics, and $C_1$ to $C_4$ aliphatics. The dehydrogenation product stream is then fed to a further separation system, typically a further distillation tower, to divide the dehydrogenation product stream into a $C_6$ recycle stream and a paraffin-rich stream comprising 2-methylpentane, 3-methylpentane, and other $C_1$ to $C_6$ paraffins. The $C_6$ recycle stream can then be recycled to the hydroalkylation step, while the paraffinic stream can be used as a fuel for the process.

After separation of the $C_6$-rich stream, the remainder of hydroalkylation reaction effluent is fed a second distillation tower to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1. The transalkylation reaction effluent can then be returned to the second distillation tower to recover the additional monocyclohexylbenzene product produced in the transalkylation reaction.

After separation in the second distillation tower, the cyclohexylbenzene is converted into phenol by a process similar to the Hock process. In this process, the cyclohexylbenzene is initially oxidized to the corresponding hydroperoxide. This is accomplished by introducing an oxygen-containing gas, such as air, into a liquid phase containing the cyclohexylbenzene. Unlike the Hock process, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217; the entire disclosure of which is incorporated herein by reference.

The effluent from the cleavage reaction comprises phenol and cyclohexanone in substantially equimolar amounts and, depending on demand; the cyclohexanone can be sold or can be dehydrogenated into additional phenol. Any suitable dehydrogenation catalyst for the dehydrogenation of cyclohexanone can be used in this reaction.

Preferably, the cyclohexanone dehydrogenation catalyst is selected from the catalyst compositions described as being useful for the first catalyst in the first conversion step of this invention.

Suitable conditions for the dehydrogenation step comprise a temperature of about 250° C. to about 700° C. and a pressure of about 0.01 atm to about 20 atm (1 kPa to 2000 kPa), such as a temperature of about 300° C. to about 450° C. and a pressure of about 1 atm to about 10 atm (100 kPa to 1000 kPa).

Provided are one or more embodiments:
A. A dehydrogenation process comprising:
  (a) providing a hydrocarbon stream comprising at least one non-aromatic six-membered ring compound and at least one five-membered ring compound;
  (b) producing a first reaction product stream comprising the step of contacting at least a portion of the hydrocarbon stream with a first catalyst comprising at least one support and at least one metal component and under conditions effective to convert at least a portion of the at least one non-aromatic six-membered ring compound to at least one aromatic compound; and
  (c) producing a second reaction product stream comprising the step of contacting at least a portion of the first reaction product stream with a second catalyst and under conditions to convert at least a portion of the at least one five-membered ring compound to at least one paraffin.
B. The process of embodiment A, wherein the first catalyst has an alpha value of less than 10.
C. The process of any one of embodiments A to B, wherein the first catalyst has an alpha value of less than 5.
D. The process of any one of embodiments A to C, wherein the second catalyst has an alpha value of greater than 10.
E. The process of any one of embodiments A to D, wherein the second catalyst has an alpha value of greater than 20.
F. The process of any one of embodiments A to E, wherein the second catalyst is a solid acid catalyst.
G. The process of any one of embodiments A to F, wherein the second catalyst comprises at least one metal component.
H. The process of embodiment G, wherein the first catalyst comprises at least one metal component selected from Groups 6 to 10 of the Periodic Table of the Elements.
I. The process of any one of embodiments A to H, wherein the first catalyst comprises at least one metal component selected from platinum, palladium, ruthenium, nickel, zinc, tin, and cobalt.
J. The process of any one of embodiments A to I, wherein the second catalyst comprises at least one material selected from an alumina, an aluminosilicate, an aluminophosphate, a silicoaluminphosphate, amorphous silica-alumina, titania, an acidic clay, a mixed metal oxide, phosphoric acid, and zirconia.
K. The process of any one of embodiments A to J, wherein the second catalyst comprises at least one molecular sieve.
L. The process of embodiment K, wherein the molecular sieve comprises at least one material selected from an aluminosilicate, an aluminophosphate, and a silicoaluminphosphate.
M. The process of any one of embodiments K to L, wherein the at least one molecular sieve comprises an aluminosilicate having a silicon to aluminum atomic ratio greater than 5:1 and less than 300:1.
N. The process of any one of embodiments K to M, wherein the at least one molecular sieve comprises an AEL, AFI, MWW, MFI, MEL, MFS, MEI, MTW, EUO, MTT, HEU, FER, and/or TON structure type molecular sieve.
O. The process of any one of embodiments K to N, wherein the at least one molecular sieve has an average pore size of about 5 to about 7 Å.
P. The process of any one of embodiments K to O, wherein the at least one molecular sieve is selected from ZSM-5 and ZSM-11.
Q. The process of any one of embodiments K to P, wherein the at least one molecular sieve has an average pore size in excess of 7 Å.
R. The process of any one of embodiments K to Q, wherein the at least one molecular sieve comprises Ultrastable Y (USY) and Zeolite Beta.
S. The process of any one of embodiments K to R, wherein the second catalyst further comprises at least one metal component selected from Groups 6 to 10 of the Periodic Table of the Elements.
T. The process of embodiment S, wherein the second catalyst comprises at least one metal component selected from platinum, palladium, ruthenium, nickel, zinc, tin, and cobalt.
U. The process of any one of embodiments A to T, wherein the conditions in the producing step (b) and producing step (c) comprise a temperature between about 200° C. and about 550° C., a pressure between about 100 and about 7,000 kPaa, and a hydrogen to hydrocarbon stream molar ratio between about 0.1 and about 10.
V. The process of any one of embodiments A to U, wherein the hydrocarbon stream is a $C_6$-rich stream comprising at least 50 wt % benzene, at least 5 wt % cyclohexane, and at least 0.1 wt % methylcyclopentane.
W. The process of embodiment V, wherein the $C_6$-rich stream is produced by:
  (i) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and benzene; and
  (ii) separating at least a portion of the hydroalkylation reaction product stream into the $C_6$-rich stream and a cyclohexylbenzene-rich stream.
X. The process of embodiment W, and further comprising:
  (iii) separating at least a portion of the second reaction product stream produced in the producing step (b) into a benzene recycle stream and a paraffin-rich stream comprising 2-methylpentane and 3-methylpentane; and
  (iv) recycling at least a portion of the benzene recycle stream to the contacting step (i).
Y. A process for producing cyclohexylbenzene, the process comprising:
  (i) contacting benzene and hydrogen in the presence of a hydroalkylation catalyst under hydroalkylation conditions effective to form a hydroalkylation reaction product stream comprising cyclohexylbenzene, cyclohexane, methyl cyclopentane, and benzene;
  (ii) separating at least a portion of the hydroalkylation reaction product stream into a $C_6$-rich stream comprising benzene, cyclohexane, and methylcyclopentane and a cyclohexylbenzene-rich stream;
  (iii) producing a first reaction product stream comprising the step of contacting at least a portion of the $C_6$-rich stream with a first catalyst comprising at least one support and at least one metal component and the contacting being conducted under conditions effective to convert at least a portion of the cyclohexane to benzene;
  (iv) producing a second reaction product stream comprising the step of contacting at least a portion of the first reaction product stream with a second catalyst and under conditions to convert at least a portion of the methylcyclopentane to at least one paraffin;

(v) separating at least a portion of the second reaction product stream produced in producing step (iv) into a benzene recycle stream and a paraffins-rich stream comprising 2-methylpentane and 3-methylpentane; and (vi) recycling at least a portion of the benzene recycle stream to the contacting step (i).

Z. The process of embodiment Y, wherein the first catalyst has an alpha value less than 10.

AA. The process of any one of embodiments Y to Z, wherein the second catalyst has an alpha value of greater than 10.

AB. The process of any one of embodiments Y to AA, wherein the first catalyst has an alpha value of less than 10 and the second catalyst has an alpha value of more than 20.

AC. The process of any one of embodiments Y to AB, wherein the hydroalkylation conditions in the contacting step (i) include a temperature between about 100° C. and about 400° C. and a pressure between about 100 and about 7,000 kPa.

AD. The process of any one of embodiments Y to AC, wherein the hydroalkylation catalyst comprises a molecular sieve of the MCM-22 family and a hydrogenation metal.

AE. The process of any one of embodiments Y to AD, wherein the conditions in the producing step (iii) comprise a temperature between about 200° C. and about 550° C., a pressure between about 100 and about 7,000 kPaa, and a hydrogen to $C_6$-rich stream molar ratio between about 0.1 to about 10.

When a stream is described as being "rich" in a specified species, it is meant that the specified species in that stream is enriched relative to other species in the same stream or composition on a weight percentage basis. For illustration purposes only, a cyclohexylbenzene-rich stream will have a cyclohexylbenzene wt % greater than any other species or component in that same stream. A "$C_6$" species generally means any species containing 6 carbon atoms.

The invention will now be more particularly described with reference to the following non-limiting Examples and the accompanying drawings.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Oxygen chemisorption measurements are obtained using the Micrometrics ASAP 2010. Approximately 0.3 to 0.5 grams of catalyst are into the Micrometrics. Under flowing helium, the catalyst is ramped from ambient to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen isotherm is collected in increments at 35° C. between 0.50 and 760 mm Hg.

Example 1

First Catalyst: Preparation and Performance of Pt/K/Silica Catalyst

A 1 wt % Pt, 1 wt % K on silica catalyst was prepared and tested for conversion of cyclohexane and methylcyclopentane. The 1 wt % Pt, 1 wt % K on silica catalyst was prepared by the following procedure. A silica extrudate (297 grams) prepared according to WO2007084440A1 was impregnated using aqueous based incipient wetness impregnation with 5.21 grams of potassium carbonate (3.0 grams of metallic potassium) combined with 283 grams of deionized water based upon total weight of the catalyst composition followed by air calcination at 540° C. After the potassium impregnation and calcination, a platinum containing 1/20" quadralobe silica extrudate was prepared using tetra-ammine Pt hydroxide (1 wt % Pt) solution using aqueous based incipient wetness impregnation by impregnating 297 grams Of 1% K/SiO2) with a solution containing 66.87 grams of tetraammine platinum hydroxide (4.486 wt % Pt) and 215 grams deionized water followed by drying at 121° C. After impregnation, the extrudate was calcined in air at 350° C. The alpha activity of this catalyst is essentially negligible. The extrudate was cut into particles of L/D=1 (length/diameter).

Excellent initial performance was obtained with the Pt/K/silica catalyst. Conversion was 55-60% and selectivity for both was 95-98% at 10 $hr^{-1}$ WHSV, 50 psig and 420° C.

In addition to the excellent initial activity and selectivity, the Pt/K/silica catalyst was also found to have excellent stability. Cyclohexane conversion was approximately 95% after 10 days-on-stream. The Pt/K/silica catalyst was tested for an additional 40 days (i.e., 50 days total) wherein the cyclohexane conversion dropped and stabilized at approximately 85%. The Pt/K/silica was also active for converting MCP, although to a mush less extent than cyclohexane at around 22%. Accordingly at day 50, the ratio of CH to MCP converted is 85 to 22 (or 3.9 to 1). Some of the products formed from conversion of MCP conversion were 2-methylpentane, 3-methylpentane, and hexane. Some lighter hydrocarbons, e.g., methane, ethane, and propane, were also observed. With the exception of hexane, all of the products from MCP are readily separable from benzene. Selectivity was excellent throughout the 50 day run at 98%.

Selectivity was calculated by normalizing all the products to 100% measured in the reactor effluent excluding MCP, CH and Bz. The selectivity data is reported as wt %.

The major products from the reaction of MCP were 2-methylpentane, 3-methylpentane, hexane, $C_1$-$C_4$, $C_5$, and heavies. Most of the products are readily separable from benzene via simple distillation. $C_{1-4}$, $C_5$ and heavies refer to hydrocarbons that have 1 to 4 carbons, five carbons, and hydrocarbons containing over 6 carbons, respectively. The $C_{1-4}$ and $C_5$ are mostly paraffins, while the heavies are mostly substituted benzenes such as xylene and bi-phenyl.

Example 2

First Catalyst: Preparation of Pt/K/Alumina Catalyst

A Pt/K/alumina catalyst was prepared and tested for conversion of cyclohexane and methylcyclopentane. The Pt/K/alumina catalyst was prepared by the following procedure. The Pt/K/$Al_2O_3$ catalyst was prepared by depositing a commercial Pt/$Al_2O_3$ catalyst with 1% K as potassium carbonate. After deposition, the extrudate was calcined in air at 350° C. The alpha activity of this catalyst is essentially negligible.

Excellent performance was also obtained with the Pt/K/alumina catalyst. Conversion was 60-70% and selectivity for both was 95-98% at 10 $hr^{-1}$ WHSV, 50 psig (344 kPa) and 420° C.

Example 3

First Catalyst: Performance of Pt/K/Silica Catalyst

The same Pt/K/silica catalyst of Example 1 was tested under different reaction and feed conditions. 250 mg of catalyst was mixed with 250 mg of 40 mesh quartz chips, and the mixture was packed into a ¼" (0.64 cm) stainless steel reactor. A liquid mixture of methylcyclopentane, cyclohexane and benzene was delivered using an ISCO pump. The liquid feed was vaporized prior to mixing with $H_2$. The mixture ($H_2$ and vaporized feed) was fed into the downflow reactor. The reaction was typically run at 500° C. and 100 psig (689 kPag) total reactor pressure, 10 WHSV (based on total liquid feed) with a $H_2$/liquid feed molar ratio of 2. The liquid feed composition was 4.4 wt % methylcyclopentane (MCP), 18.5 wt % cyclohexane (CH), and 77.1 wt % benzene (Bz).

Prior to the introduction of the liquid feed, the catalyst was pretreated with 50 standard cubic centimeters per minute (sccm) $H_2$ at 100 psig (689 kPag) by ramping reactor temperature from room temperature to 460° C. at 2° C./min; the reactor temperature was held at 460° C. for 2 hours under the same $H_2$ flow and pressure to reduce the platinum on the catalyst to the metallic state.

The effluent from the reactor was sampled using a Valco sampling valve, and the sample was sent to an on-line GC equipped with a FID detector for analysis. All hydrocarbons were quantified and the results were normalized to 100%. $H_2$ was not included in the analysis.

The conversion of cyclohexane was over 98% after 120 hrs time-on-stream. The selectivity for converting cyclohexane to benzene is very high (consistently over 96 to 98%). The high conversion of cyclohexane is desirable in the two catalyst configuration since un-reacted cyclohexane from the first reaction product will be converted to byproducts such as $C_1$-$C_5$ light olefins and alkylaromatics in the second reaction product which leads to a lower recovery of cyclohexane.

Example 4

First Catalyst Performance of Pt/Silica Catalyst Using Arginine as Dispersant Other catalysts such as Pt/SiO$_2$ prepared in the presence of arginine are also effective in converting cyclohexane to benzene with high selectivity.

A 1% Pt/SiO$_2$ catalyst was prepared by first dissolving 11.2 g of tetraamine platinum hydroxide in 61.1 g of deionized water to make a solution containing 4.49 wt % of Pt. The solution was added dropwise to 50.0 g of silica (Sigma-Aldrich Davison grade 62, 60-200 mesh, 150 angstrom), and the resulting mixture was mixed well. The sample was dried at 120° C. for 2 hrs. 10 g of the dried sample was then calcined by ramping oven temperature at a rate of 3° C./min to 350° C. and maintaining oven temperature at 350° C. for 16 hrs in 300 sccm of air. The calcined sample was denoted as 1% Pt/SiO$_2$.

The conversion of cyclohexane was between 80 and 90% which is not as high as the Pt/K/silica in Example 3 under identical conditions. Nevertheless, it still shows considerable activity for cyclohexane conversion to benzene. Of course, the conversion of cyclohexane can further be increased by optimizing reaction conditions, e.g., higher reaction temperatures or lower WHSVs.

Example 5

Second Stage Catalyst Performance of Pt/ZSM5/Silica

The effluent from the 1$^{st}$ stage may be converted over an acidic catalyst in the 2$^{nd}$ stage. An example of an acidic catalyst which is effective in conversion of methylcyclopentane is comprised of 0.1 wt % Pt/ZSM5/SiO$_2$ with an alpha activity is 70. The catalyst was tested with a feed which is comprised of 3% MCP/97% Benzene. It was also tested with a feed which is comprised of 3% cyclohexane/97% benzene.

The catalyst showed initial conversion of 39% at 460° C. and 50 psig reactor pressure and 20 hr$^{-1}$ WHSV with the 3% methylcyclopentane and 97% benzene feed. Interestingly, the catalyst showed only 13% conversion when the same catalyst was tested at the same condition but with the 3% cyclohexane and 97% benzene feed. The relative reaction rate of methylcyclopentane to cyclohexane is approximately 3 to 1. This contrasts with the first stage catalyst, which had a relative reaction rate MCP to CH of approximately 1 to 3.9. The main products from conversion of methylcyclopentane or cyclohexane over the Pt ZSM5/SiO$_2$ catalyst are $C_1$-$C_5$ light saturates and alkylaromatics.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A dehydrogenation process comprising:
   (a) providing a hydrocarbon stream comprising at least one non-aromatic six-membered ring compound and at least one five-membered ring compound;
   (b) producing a first reaction product stream comprising the step of contacting at least a portion of the hydrocarbon stream with a first catalyst having an alpha value of less than 10 comprising at least one support and at least one metal component, and under conditions effective to convert at least a portion of the at least one non-aromatic six-membered ring compound to at least one aromatic compound; and
   (c) producing a second reaction product stream comprising the step of contacting at least a portion of the first reaction product stream with a second catalyst having an alpha value of greater than 10 and under conditions to convert at least a portion of the at least one five-membered ring compound to at least one paraffin, the second catalyst comprises at least one molecular sieve selected from the group consisting of AEL, AFI, MWW, MFI, MEL, MFS, MEI, MTW, EUO, MTT, HEU, FER, and/or TON structure type molecular sieve.

2. The process of claim 1, wherein the first catalyst in step (b) has an alpha value of less than 5.

3. The process of claim 1, wherein the second catalyst in step (c) has an alpha value of greater than 20.

4. The process of claim 1, wherein the second catalyst in step (c) is a solid acid catalyst.

5. The process of claim 1, wherein the second catalyst in step (c) comprises at least one metal component.

6. The process of claim 5, wherein the first catalyst in step (b) comprises at least one metal component selected from the group consisting of Groups 6 to 10 of the Periodic Table of the Elements.

7. The process of claim 1, wherein the first catalyst in step (b) comprises at least one metal component selected from the group consisting of platinum, palladium, ruthenium, nickel, zinc, tin, and cobalt.

8. The process of claim 1, wherein the second catalyst in step (c) further comprises at least one material selected from an alumina, an aluminosilicate, an aluminophosphate, a silicoaluminphosphate, amorphous silica-alumina, titania, an acidic clay, a mixed metal oxide, phosphoric acid, and zirconia.

9. The process of claim 1, wherein the at least one molecular sieve comprises an aluminosilicate having a silicon to aluminum atomic ratio greater than 5:1 and less than 300:1.

10. The process of claim 1, wherein the at least one molecular sieve has an average pore size of about 5 to about 7 Å.

11. The process of claim 1, wherein the at least one molecular sieve is selected from ZSM-5 and ZSM-11.

12. The process of claim 1, wherein the at least one molecular sieve has an average pore size in excess of 7 Å.

13. The process of claim 1, wherein the at least one molecular sieve comprises Ultrastable Y (USY) and Zeolite Beta.

14. The process of claim 1, wherein the second catalyst in step (c) further comprises at least one metal component selected from Groups 6 to 10 of the Periodic Table of the Elements.

15. The process of claim 14, wherein the second catalyst in step (c) comprises at least one metal component selected from platinum, palladium, ruthenium, nickel, zinc, tin, and cobalt.

16. The process of claim 1, wherein the conditions in the producing step (b) and producing step (c) comprise a temperature between about 200° C. and about 550° C., a pressure between about 100 and about 7,000 kPaa, and a hydrogen to hydrocarbon stream molar ratio between about 0.1 and about 10.

17. The process of claim 1, wherein the hydrocarbon stream is a $C_6$-rich stream comprising at least 50 wt % benzene, at least 5 wt % cyclohexane, and at least 0.1 wt % methylcyclopentane.

18. The process of claim 17, wherein the $C_6$-rich stream is produced by:
(i) contacting benzene and hydrogen in the presence of a hydroalkylation catalyst under hydroalkylation conditions effective to form a hydroalkylation reaction product stream comprising cyclohexylbenzene, cyclohexane, methylcyclopentane, and benzene; and
(ii) separating at least a portion of the hydroalkylation reaction product stream into the $C_6$-rich stream and a cyclohexylbenzene-rich stream.

19. The process of claim 18, the process further comprising:
(iii) separating at least a portion of the second reaction product stream produced in the producing step (b) into a benzene recycle stream and a paraffin-rich stream comprising 2-methylpentane and 3-methylpentane; and
(iv) recycling at least a portion of the benzene recycle stream to the contacting step (i).

* * * * *